United States Patent [19]

Black et al.

[11] Patent Number: 5,057,504
[45] Date of Patent: Oct. 15, 1991

[54] 1-HETEROCYCLIC BICYCLO-OCTANES

[75] Inventors: Malcolm H. Black; John A. Wyatt; John B. Weston; John P. Larkin; Ian H. Smith; David A. Pulman, all of Berkhamsted, England

[73] Assignee: The Wellcome Foundation Limited, London, England

[21] Appl. No.: 395,287

[22] Filed: Aug. 16, 1989

Related U.S. Application Data

[63] Continuation of Ser. No. 41,963, Apr. 24, 1987, abandoned.

[30] Foreign Application Priority Data

Apr. 25, 1986 [GB] United Kingdom ............... 8610130
Apr. 25, 1986 [GB] United Kingdom ............... 8610131

[51] Int. Cl.$^5$ ............... A01N 55/00; A01N 43/40; C07D 211/08; C07D 213/24
[52] U.S. Cl. ............... 514/63; 514/149; 514/321; 514/338; 514/427; 514/452; 546/14; 546/197; 546/270; 548/406; 548/542; 548/543; 548/556; 548/557; 548/558; 548/560; 548/561; 548/562
[58] Field of Search ............... 546/270, 14, 197; 514/338, 452, 63, 14.9, 321, 427, 452; 548/406, 542, 543, 556, 557, 558, 560, 561, 562

[56] References Cited

U.S. PATENT DOCUMENTS 3,415,846 12/1968 Kesslin ............... 549/363
3,686,224 8/1972 Deffner ............... 549/363
4,355,037 10/1982 Strupczewski et al. ............... 514/321
4,507,292 3/1985 Heywang et al. ............... 546/197

FOREIGN PATENT DOCUMENTS 152229 8/1985 European Pat. Off.
0243184 10/1987 European Pat. Off. ............... 549/363
2757483 6/1979 Fed. Rep. of Germany ............... 546/197

Primary Examiner—C. Warren Ivy
Assistant Examiner—Amelia A. Owens
Attorney, Agent, or Firm—Nixon & Vanderhye

[57] ABSTRACT

Pesticidal bicyclo-octanes are of the formula

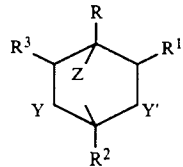

where R is a substituted or unsubstituted aliphatic or aromatic group, R' and $R^3$ are H or a substituted or unsubstituted aliphatic or aromatic group, $R^2$ is a substituted or unsubstituted heterocyclic group containing at least one ring nitrogen and is preferably a 3- or 4- pyridyl group, Z is $CH_2CH_2$, $CH_2O$—$CH_2S$ or $COCH_2$ or $CH(OR^5)CH_2$ where $R^5$ is H, alkyl, acyl or carbamoyl at Y and Y' are O or $S(O)_m$ where m is 0, 1 or 2.

Various methods for their preparation are described.

9 Claims, No Drawings

1-HETEROCYCLIC BICYCLO-OCTANES

This is a continuation of application Ser. No. 07/041,963, filed Apr. 24, 1987, now abandoned.

The present invention relates to novel chemical compounds having pesticidal activity, to methods for their preparation, to compositions containing them and to their use in the control of pests. More particularly the invention relates to a class of heterobicycloalkanes.

European Patent Application number 152229 discloses 1,4-bis-substituted-2,6,7-trioxabicyclo[2.2.2]octanes having pesticidal activity. It has now been discovered that compounds wherein the 1-position of the bicyclooactane ring is substituted by particular heterocyclic groups have interesting pesticidal activity.

Accordingly the present invention provides a compound of the formula (I);

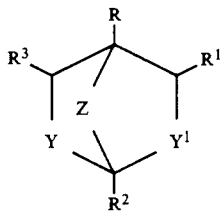

wherein R is $C_{2-10}$ alkyl, alkenyl or alkynyl, each optionally substituted by or methyl substituted by, cyano, halogen, $C_{3-4}$ cycloalkyl, $C_{1-4}$ alkoxy or a group $S(O)mR^4$ where $R^4$ is $C_{1-4}$ alkyl optionally substituted by halogen and m is 0, 1 or 2, or R is $C_{3-10}$ cycloalkyl, $C_{4-10}$ cycloalkylalkyl, $C_{4-10}$ cycloalkenyl or phenyl, each optionally substituted by $C_{1-4}$ alkoxy, $C_{1-3}$ alkyl, $C_{2-4}$ alkynyl, halogen, cyano or a group $S(O)mR^4$ as hereinbefore defined; $R^1$ is hydrogen, $C_{1-3}$ alkyl, $C_{2-3}$ alkenyl or alkynyl, each optionally substituted by halo, cyano, $C_{1-4}$ alkoxy, alkyl carbalkoxy containing up to 6 carbon atoms or a group $S(O)m$ $R^4$ as hereinbefore defined, or $R^1$ is cyano, $CO_2 R^4$ wherein $R^4$ is as hereinbefore defined or gem dimethyl; or $R^1$ and R and the carbon atoms to which they are attached form a $C_{5-7}$ carbocyclic ring optionally substituted by cyano, halogen, $C_{1-3}$ alkyl, $C_{2-3}$ alkoxy or alkenyl; $R^2$ is an optionally substituted 5 or 6 membered ring containing a nitrogen atom; and optionally one to three further hetero atoms selected from nitrogen, oxygen and sulphur; and $R^3$ is hydrogen, cyano, $C_{1-3}$ alkyl, $C_{2-3}$ alkenyl or alkynyl, each optionally substituted by cyano, $C_{1-4}$ alkoxy, halo or a group $S(O)m$ $R^4$ as hereinbefore defined, Y and $Y^1$ are the same or different and are each selected from oxygen or $S(O)m$ where m is 0, 1 or 2; Z is $CH_2CH_2$, $CH_2O$ or $CH_2S$, or Z is —CO.$CH_2$— or —CH($OR^5$)$CH_2$— wherein $R^5$ is hydrogen, $C_{1-4}$ alkyl, $C_{1-4}$ acyl or $C_{1-3}$ carbamoyl.

The compounds of the formula (I) may exist in tautomeric forms in some cases, in which case the present invention provides individual tautomers and mixtures thereof.

Suitably R is propyl, butyl, pentyl, $C_{2-5}$ alkenyl or alkynyl, $C_{5-7}$ cycloalkyl or phenyl, each optionally substituted by one to three fluoro, chloro or bromo. Most suitably R is n-propyl, i-propyl, n-butyl, i-butyl, sec-butyl, t-butyl, cyclopentyl, cyclohexyl or phenyl and preferably R is n-propyl, n-butyl, i-butyl, cyclohexyl or phenyl.

Suitably $R^1$ is hydrogen, cyano, or methyl or ethyl, each optionally substituted by cyano, methoxy, methylthio, chloro, bromo or fluoro. Most suitably $R^1$ is hydrogen, methyl, cyano, trifluoromethyl or ethyl. Preferably $R^1$ is hydrogen.

$R^2$ is a saturated or a partially or fully unsaturated ring, preferably a fully unsaturated ring such as pyridine. Other suitable rings include piperidine, pyrimidine, imidazole, pyridazine, pyrazine, pyrrolidine, pyrrole, pyrazole, thiazole, oxazole and isoxazole. Nitrogen or sulphur atoms present in the ring may have oxygen atoms attached, i.e. N-oxides sulphones or sulphoxides may be formed. Alternatively, the nitrogen atom may be substituted by hydrogen, benzyl, $C_{1-4}$ alkyl or a group $C(O)R^6$ wherein $R^6$ is $C_{1-4}$ alkyl, alkoxy, or an amino group optionally substituted by one or two $C_{1-4}$ alkyl groups, or it can be present as a quaternary ammonium ion.

Suitable substituents on the group $R^2$ include hydroxy; oxo; halo; cyano; imino or amino optionally substituted by $C_{1-4}$ alkyl or acyl or $C_{1-6}$ carbalkoxy; azido; nitro; formyl; $C_{1-6}$ carbalkoxy; thiocyanate; $C_{1-4}$ acyl; $C_{1-4}$ acyloxy, $C_{1-4}$ alkoxyiminomethylene; $C_{1-4}$ acyloxyiminomethylene; or $C_{1-3}$ alkyl or alkoxy each optionally substituted by halo; or $C_{2-3}$ alkenyl or ethynyl each optionally substituted by cyano, a $C_{1-9}$ aliphatic group optionally substituted by hydroxy, $C_{1-4}$ alkoxy, $C_{1-4}$ acyloxy, $C_{1-4}$ acylthio or halogen, a group —$CO.R^7$ where $R^7$ is a $C_{1-6}$ hydrocarbyl or hydrocarbyloxy group or an amino group optionally substituted by one or two $C_{1-4}$ alkyl groups; or by a silyl group substituted by three $C_{1-4}$ alkyl groups or two $C_{1-4}$ alkyl groups and a phenyl group. The halo substituent may be fluoro, chloro, bromo or iodo. Suitably there are up to three substituents chosen from halo, trifluoromethyl, ethynyl optionally substituted by a silyl group substituted by three $C_{1-4}$ alkyl groups or two $C_{1-4}$ alkyl groups and a phenyl group or by a $C_{1-4}$ alkyl group optionally substituted by $C_{1-4}$ alkoxy. Preferably $R^2$ is an optionally substituted 3- or 4-pyridyl group.

By the term "hydrocarbyl" group is meant alkyl, alkenyl (including cyclic alkyl and alkenyl, and alkyl and alkenyl substituted by cyclic alkyl and alkenyl), alkynyl, aryl and aralkyl groups. "Hydrocarbyloxy" means a hydrocarbyl group as defined where linked to oxygen.

Suitably $R^3$ is hydrogen.
Suitably Z is —$CH_2S$—, —$CH_2O$— or —$CH_2CH_2$—. Most suitably Z is —$CH_2S$— or —$CH_2O$—. Preferably Z is —$CH_2O$—, the heteroatom being adjacent to the carbon atom substituted by $R^2$.

Suitably Y and $Y^1$ are both oxygen.

One group of compounds of the formula (I) is that of the formula (Ia):

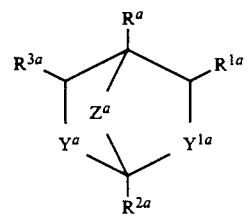

wherein $R^a$ is $C_{2-10}$ alkyl, alkenyl or alkynyl, each optionally substituted by cyano, halogen, $C_{1-4}$ alkoxy or a group $S(O)mR^{4a}$ where $R^{4a}$ is $C_{1-4}$ alkyl and m is 0, 1 or 2, or $R^a$ is $C_{3-10}$ cycloalkyl, $C_{4-10}$ cycloalkenyl or phenyl, each optionally substituted by $C_{1-4}$ alkoxy, $C_{1-3}$ alkyl, $C_{2-4}$ alkynyl, halogen, cyano or a group $S(O)m-R^{4a}$; $R^{1a}$ is hydrogen, $C_{1-3}$ alkyl, $C_{2-3}$ alkenyl or alkynyl, each optionally substituted by halo, cyano, $C_{1-4}$ alkoxy, alkyl, carbalkoxy containing up to 6 carbon atoms or a group $S(O)m$ $R^{4a}$ as hereinbefore defined, or $R^{1a}$ is cyano or gem dimethyl; or $R^{1a}$ and $R^a$ and the carbon atoms to which they are attached form a $C_{5-7}$ carbocyclic ring optionally substituted by $C_{1-3}$ alkyl, $C_{2-3}$ alkoxy or alkenyl; $R^{2a}$ is an optionally substituted 5 or 6 membered ring containing a nitrogen atom; and optionally one further hetero atom selected from nitrogen, oxygen and sulphur and $R^{3a}$ is hydrogen, cyano, $C_{1-3}$ alkyl, $C_{2-3}$ alkenyl or alkynyl, each optionally substituted by cyano, $C_{1-4}$ alkoxy, halo or a group $S(O)m$ $R^{4a}$ as hereinbefore defined, $Y^a$ and $Y^{1a}$ are the same or different and are each selected from oxygen or $S(O)m$ where m is 0, 1 or 2; $Z^a$ is $CH_2CH_2$, $CH_2O$, $CH_2S$, or $Z^a$ is —CO.CH$_2$— or —CH(OR$^{5a}$)CH$_2$— wherein $R^{5a}$ is hydrogen, $C_{1-4}$ alkyl, $C_{1-4}$ acyl or $C_{1-3}$ carbamoyl.

Preferred compounds of the present invention include:

1-(6-Chloro-3-pyridyl)-4-n-propyl-2,6,7-trioxabicyclo[2.2.2]octane 1-(6-Chloro-N-oxo-3-pyridyl)-4-n-propyl-2,6,7-trioxabicyclo[2.2.2]octane 1-(6-Chloro-3pyridyl)-4-cyclohexyl-2,6,7-trioxabicyclo[2.2.2]octane 4-n-Propyl-1-(4-pyridyl)-2,6,7-trioxabicyclo[2.2.2]octane 1-(N-Oxo-4-pyridyl)-4-n-propyl-2,6,7-trioxabicyclo[2.2.2]octane 4-Cyclohexyl-1-(4-pyridyl)-2,6,7-trioxabicyclo[2.2.2]octane 1-(6-Iodo-3-pyridyl)-b 4-n-propyl-2,6,7-trioxabicyclo[2.2.2]octane 1-(2,6-Dichloro-4-yridyl)-4-n-propyl-2,6,7-trioxabicyclo[2.2.2]octane 1-(4-Ethynyl-3-pyridyl)-4-n-propyl-2,6,7-trioxabicyclo[2.2.2]octane 4-Propyl-1-[6-(2-trimethylsilylethynyl)-3-pyridyl]-2,6,7-trioxabicyclo [2.2.2]octane 1-[6-(3-Methoxyprop-1-ynyl)-3-pyridyl]-4-n-propyl-2,6,7-trioxabicyclo [2.2.2]octane 4-Phenyl-1-(4-pyridyl)-2,6,7-trioxabicyclo[2.2.2]octane 4-Cyclohexyl-1-(6-iodo-3-pyridyl)-2,6,7-trioxabicyclo[2.2.2]octane In a further aspect, the present invention provides a process for the preparation of a compound of the formula (I). The process for the preparation of a compound of the formula (I) may be a method known in the art for preparing analogous compounds, for example (i) when Y and $Y^1$ are oxygen and Z is $CH_2O$, by the cyclisation of a compound of the formula (II):

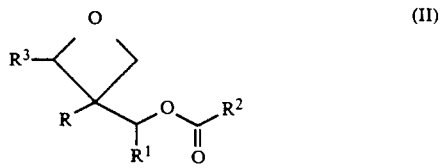

wherein R to $R^3$ are as hereinbefore defined, in the presence of an acid catalyst. Boron trifluoride etherate is a particularly preferred acid catalyst for this cyclisation, which will normally be carried out in an inert solvent, such as a halogenated hydrocarbon, conveniently dichloromethane, at below ambient temperature, for example between −100 and 0° C. and conveniently between −70° and −50° C., The compounds of the formula (II) may be prepared by the reaction of compounds of the formulae (III) and (IV):

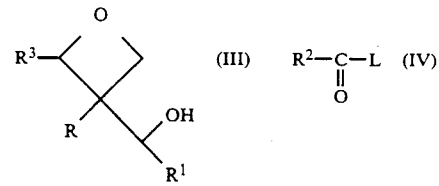

where R to $R^3$ are as hereinbefore defined and L is a leaving group such as halo or hydroxy. This reaction conveniently takes place under conditions well known to those skilled in the art, for example when L is halo in an inert solvent in the presence of base at a non-extreme temperature and when L is hydroxy in an inert solvent in the presence of a condensing agent at a non extreme temperature. When L is halo halogenated hydrocarbons, such as dichloromethane, are particularly suitable inert solvents, pyridine is a preferred base; when L is hydroxy, dimethylformamide is a suitable solvent, dicyclohexylcarbodiimide is a preferred condensing agent; and the reaction will conveniently be carried out at between −50° and 100° C., preferably between 0° and 25° C.

The compounds of the formula (III) may in turn be prepared from compounds of the formula (V):

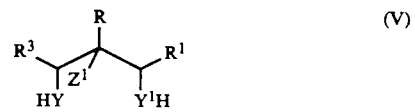

wherein Y and $Y^1$ are oxygen and $Z^1$ is $CH_2OH$, by reaction with diethyl carbonate in the presence of a strong base, for example potassium hydroxide, in a polar solvent, such as an alcohol, for example ethanol, at an elevated temperature, for example between 50° and 100° C. This is a preferred method of making compounds of the formula (III) wherein $R^1$=$CF_3$ or $R^1$=H.

The compounds of the formula (III) may alternatively be prepared by the reaction of a Grignard reagent $R^1MgHal$ with a compound of the formula (VI)

wherein R, $R^1$ and $R^3$ are as hereinbefore defined and Hal is a halogen atom such as bromine or iodine. This reaction is conveniently carried out in an inert solvent, suitably an ether (for example diethyl ether), at a non-extreme temperature, for example between −50° and 50° C. and preferably between −10° and 10° C. The compounds of the formula (VI) may be prepared by oxidation of the compounds of the formula (III) wherein $R^1$ is hydrogen by using oxalyl chloride and dimethyl suphoxide in a inert solvent, such as a halogenated hydrocarbon, for example dichloromethane, followed by a base such as triethylamine or by using pyridinium chlorochromate in an inert solvent, such as a halogenated hydrocarbon, for example dichloromethane.

The triol of the formula (V) wherein Y and $Y^1$ are oxygen and Z is $CH_2OH$ and $R^1$ and $R^3$ are hydrogen may be prepared by the reaction of an aldehyde $RCH_2CHO$ with formaldehyde in the presence of a strong base, for example calcium hydroxide, at a non-extreme temperature i.e. between 0° and 100° C. and conveniently at 50° to 70° in aqueous solution.

The triol of the formula (V) wherein $R^1$ and/or $R^3$ are other than hydrogen may be prepared from the corresponding triol where $R^1$ and/or $R^3$ are hydrogen via a protected aldehyde which is reacted with a reagent, such as a Grignard reagent, which is suitable for lengthening the carbon chain followed by deprotection.

In certain cases, it may be convenient to prepare triol derivatives where $R^1$ and $R^3$ are hydrogen and one of the hydroxy groups is protected, by reduction of an ester of the formula (VII):

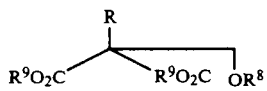
(VII)

wherein $R^8$ is a protecting group such as benzyl and $R^9$ is $C_{1-4}$ alkyl. This reduction is suitably carried out by a complex hydride such as lithium aluminium hydride in an inert solvent, conveniently an ether. The compound of the formula (VII) may be prepared from the corresponding compound $RCH(CO_2R^9)_2$ by reaction with a compound $XCH_2OR^8$, where X is a leaving group such as a halogen, in the presence of a strong base, such as sodium hydride.

(ii) compounds of the formula (I) wherein $R^1$ is trifluoromethyl and $R^3$ is hydrogen, can be prepared by the reduction of a compound of the formula (VIII):

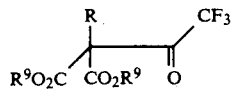
(VIII)

wherein R, and $R^9$ are as hereinbefore defined. This reduction is suitably carried out by means of a complex hydride, such as lithium aluminium hydride in an inert solvent such as an ether, for example diethyl ether.

The compounds of the formula (VIII) are conveniently prepared by the reaction of a compound $RCH(CO_2R^9)_2$ wherein R and $R^9$ are as hereinbefore defined with trifluoroacetic anhydride. This reaction is conveniently carried out in the presence of a strong base, such as a metal hydride in a non-polar solvent, for example an aromatic hydrocarbon such as benzene or toluene.

(iii) by the reaction of a compound analogous to that of the formula (V) and wherein R, $R^1$, $R^3$, Y, and $Y^1$ are as defined in relation to formula (I) and $Z^1$ is $CH_2OH$ with an orthocarboxylate of the formula $R^2 C(OR^{10})_3$ wherein $R^2$ is as hereinbefore defined and $R^{10}$ is $C_{1-4}$ alkyl, phenyl or $C_{7-8}$ aralkyl. Suitably $R^{10}$ is methyl or ethyl, preferably methyl. The reaction is normally carried out in the presence of an acid such as a mineral acid, conveniently hydrochloric acid or a sulphonic acid derivative, such as toluene sulphonic acid, or an acid resin, or in the presence of a trialkylamine, such as triethylamine, at an elevated temperature, for example between 50° and 200° C., conveniently between 120° and 170° C. The reaction may conveniently be carried out in the absence of a solvent but a suitable solvent may be added if desired. The preparation of such orthocarboxylates is described in U.S. Pat. No. 4,772,624. (EP-A-152229), U.S. Pat. No. 4,942,173 (EP-A-211598) and U.S. Pat. No. 4,985,582 (EP-A-216625) which are incorporated by reference herein.

It is often convenient to prepare compounds of the formula (I) by interconversion from other compounds of the formula (I), for example:

(i): when it is desired to prepare a compound of the formula (I) wherein the substituent on $R^2$ is substituted ethynyl by the reaction of the corresponding unsubstituted alkynyl compound with a compound Hal $R^{11}$ wherein Hal is halogen and $R^{11}$ is the substituent on the ethynyl group. This reaction is particularly suitable for the preparation of those compounds wherein $R^{11}$ is a $C_{1-4}$ alkyl group or a group $COR^{12}$ wherein $R^{12}$ is a $C_{1-6}$ alkoxy group. The reaction is normally carried out in the presence of a strong base, such as an alkyllithium conveniently butyllithium in an inert solvent, such as an ether, for example tetrahydrofuran, at a non-extreme temperature, for example between −50° and 50° C. and conveniently between −10° and 30° C. The starting material, i.e. the unsubstituted alkynyl compound may be prepared as described below.

(ii) when it is desired to prepare a compound of the formula (I) wherein the substituent on $R^2$ is ethynyl by the desilylation of the corresponding compound of the formula (I) wherein the alkynyl group is substituted by a tri-$C_{1-4}$ alkylsilyl group. This reaction may be carried out by methods well known to those skilled in the art, for example by reaction with tetrabutyl-ammonium fluoride in an ether, such as tetrahydrofuran, at a non-extreme temperature, for example between 0° and 70° C. and conveniently at room temperature.

(iii) N-oxides, sulphones and sulphoxides may be prepared by oxidation of the corresponding unoxidised heterocycle. This may be carried out by methods well known to those skilled in the art, for example by reaction with a peracid, such as chloroperbenzoic acid, in an inert solvent, such as a halogenated hydrocarbon, conveniently chloroform or dichloromethane, at a non extreme temperature, i.e. between −20° and 100°, suitably between 0° and 50° and conveniently between 20° and 30°.

(iv) when it is required to prepare a compound of the formula (I) wherein the substituent on $R^2$ is ethynyl optionally substituted by a group $R^{13}$ wherein $R^{13}$ is a $C_{1-9}$ aliphatic group optionally substituted by hydroxy, $C_{1-4}$ alkoxy, $C_{1-4}$ acyloxy, $C_{1-4}$ acylthio or halogen or $R^{13}$ is silyl substituted by three $C_{1-4}$ alkyl groups or two $C_{1-4}$ alkyl groups and a phenyl group, by the reaction of the corresponding compound which contains iodo in place of —C≡C—$R^{13}$ with a compound HC≡C$R^{13}$ wherein $R^{13}$ is as hereinbefore defined. This reaction is carried out in the presence of a suitable palladium catalyst well known to those skilled in the art for this type of reaction, for example bis-triphenylphosphine palladium dichloride, and a catalytic amount of a cuprous halide, such as cuprous iodide. The reaction will normally be carried out in the presence of basic solvent such as diethylamine or triethylamine at a non-extreme temperature, for example between −50° and 100° C. and conveniently at room temperature.

The compounds of Formula (I) may be used to control anthropods such as insect and acarine pests. Certain compounds of the formula (I) have been found to have "knockdown" activity against *Musca domestica* and *Culex quinquefasciatur* in addition to kill activity. The compounds of the present invention may control arthropods by virtue of any one of or more than one of their killing, knockdown, or behaviour modifier (e.g. bit inhibition, antifeedant or activator) activity or by acting as development inhibitors. However, the present invention is not limited in anyway by the mode of action of the compounds.

The types of arthropod pests controlled include agricultural pests (i.e. pests of food, fibre, fabric, food additives, flavouring, plants of medical importance, horticultural plants) veterinary pests or parasitic and nuisance value or capable of disease transmission, forestry pests, pests of stored commodities (be they food, textiles, timber or other products of plant or animal origin) and pests associated with transmission of disease in man or a nuisance to man.

The compounds of Formula (I) may be used for such purposes by application of the compounds themselves or in diluted form. The precise nature of the formulation will normally depend on the nature of the compound and the pest to be controlled. Thus the compounds can be applied as a dip, spray, lacquer, foam, dust, powder, aqueous suspension, past, gel, shampoo, grease, combustible solid, vapour emanator, combustible coil, bait, wettable powder, granule, aerosol, microcapsule, emulsifiable concentrate, oil suspensions, oil solutions, pressure- pack, impregnated article or pour on formulation. Dip concentrates are not applied per se, but diluted with water and the animals immersed in a dipping bath containing the dip wash. Sprays may be applied by hand or by means of a spray race or arch. The animal, plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material against with animals rub and transfer the material to their skins. Pour-on formulations are dispensed as a unit of liquid of small volume on to the backs of animals such that all or most of the liquid is retained on the animals. Vapour emanators disperse the compounds into the immediate atmosphere as vapour or small particles.

The compounds of Formula (I) may be formulated either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution. Dusts and powders comprise the compound of Formula (I) in intimate admixture with a powdered solid inert carrier for example suitable clays, kaolin, talc, mica, chalk, gypsum, kieselguhr, vegetable carriers, starch and diatomaceous earths. Granules comprise the compound of Formula (I) absorbed onto a porous granular material (e.g. pumice) or onto plastics materials for a controlled release formulation.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosens, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates but may also be cationic or amphoteric surface active agents.

Wettable powders comprise an inert solid carrier, one or more surface active agents, and optionally stabilisers and/or anti-oxidants.

Emulsifiable concentrates comprise emulsifying agents, and often an organic solvent, such as kerosens, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion. Liquid formulations may be obtained by dissolving a compound of the Formula (I) in a suitable solvent (aliphatic, aromatic or polar).

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes, butane, propane or water or the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such Articles include impregnated collars, tags, bands sheets and strips suitably attached to appropriate parts of the body. Suitably the plastics material is a polyvinyl chloride (PVC).

The concentration of the compound of Formula (I) to be applied to an animal will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% except for undiluted formulations such as pour-on formulations which in general will be deposited at a concentration in the range from 0.1 to 20.0% and preferably 0.1 to 10%. The compounds of formula (I) are also of use in the protection and treatment of plant species, in which case an effective insecticidal or acaricidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 Kg/Ha and preferably between 0.01 and 1 Kg/Ha. Typical formulations for agricultural use contain between 0.0001% and 50% of a compound of formula (I) and conveniently between 0.1 and 15% by weight of a compound of the formula (I).

Particular crops include cotton, wheat, maize, rice, sorghum, soya, vines, tomatoes, potatoes, fruit trees and spruce.

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, certain compounds of formula (I) have activity against other arthropod pests including *Tetranychus urticae, Plutella xylostella,* Culex spp. *Myzus persicae, Sitophilus granarius* and *Blattella germanica*) The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Tribolium, Sitophilus, Diabrotica, Anthonomus or Anthrenus spp.), Lepidoptera (e.g. Ephestia, Plutella, Chilo, Heliothis, Spodoptera or Tineola spp.), Diptera (e.g. Musca, Aedes, Culex, Glossina, Simulum, Stomoxys, Haematobia, Tabanus, Hydrotaea, Lucilia, Chrysomia, Callitroga, Dermatobia, Hypoderma, Liriomyza and Melophagus spp.), Phthiraptera (Malophaga e.g. Damalina spp. and Anoplura e.g. Linognathus and Haematopinus spp.), Hemiptera (e.g. Aphis, Bemisia, Aleurodes, Nilopavata, Nephotettix or Cimex spp.), Orthoptera (e.g. Schistocerca, Locusta or Acheta spp.), Dictyoptera (e.g., Blattella, Periphlaneta or Blatta spp.), Hymenoptera (e.g., Solenopsis or Monomorium spp.), Isoptera (e.g., Reticulitermes spp.), Siphonaptera (e.g. Ctenocephalides or Pulex spp.), Tysanura (e.g. Lepisma spp.), Dermaptera (e.g. Forficula spp.) and Psocoptera (e.g. Peripsocus spp.).

Acarine pests include ticks, e.g. members of the genera Boophilus, Rhipicephalus, Amblyomma, Hyalomma, Ixodes, Haemaphysalis, Dermocentor and Anocentor, and mites and manges such as Tetranychus, Panonychus, Psoroptes, Psorergates, Chorioptes and Demodex spp.

Compounds of the invention may be combined with one or more other biologically active ingredients such as other insecticides and acarocides (for example pyrethroids, carbamates, organophosphates benzyl ureas, avermectins and pyrethrins) and/or with attractants and the like and/or fungicides and/or antibiotics. Furthermore, it has been found that the activity of the compounds of the invention may be enhanced by the addition of a synergist or potentiator, for example: one of the oxidase inhibitor class of synergists, such as piperonyl butoxide or NIA 16388; a second compound of the invention; or a pyrethroid pesticidal compound. When an oxidase inhibitor synergist is present in a formula of the invention, the ratio of synergist to compound of Formula (I) will be in the range 25:1–1:25 e.g. about 10:1.

Stablisers for preventing any chemical degradation which may occur with the compounds of the invention include, for example, antioxidants (such as tocopherols, butylhydroxyanisole and butylhydroxytoluene) and scavengers (such as epichlorphydrin).

The following Examples illustrate, in a non-limiting manner, preferred aspects of the invention. All temperatures are in degrees Celsius.

EXAMPLE A

4-Ethyl-1-(3-pyridyl)-2,6,7-trioxabicyclo[2.2.2]octane (i) To a stirred mixture of n-valeraldehyde (172 g) and water (2.1) was added solid calcium hydroxide (112 g) and formaldehyde solution (1.4 l. of 40% aqueous solution). The reaction temperature was maintained below 40° and the addition took about 45 minutes. The mixture was then maintained at 60° for 5 hours. The reaction mixture was filtered through Kieselguhr and the filtrates were evaporated in vacuo. The residue was treated with hot methanol (2.1) and the mixture was filtered through Kieselguhr. The filtrates were evaporated in vacuo. A viscous oily product was obtained (458 g.) and was purified as follows:

A solution of the crude product and acetic acid (200 ml.) was stirred at room temperature. Acetic anhydride (1.2.1.) was added over 4 hours. The temperature rose to 65°. Stirring was continued for 12 hours. The reaction mixture was added over 3 hours to cold water (3.1) with stirring. Stirring was continued for 3 hours. The aqueous mixture was extracted with diethyl ether. The ether extracts were washed with aqueous sodium hydrogen carbonate solution and then with brine. The extracts were dried over anhydrous magnesium sulphate and then evaporated in vacuo.

Distillation gave 2-n-propyl-2-hydroxymethyl-propan-1,3-diol triacetate (238 g.), a colourless oil (b.pt.120°–140°, 1.5 mm).

Nuclear magnetic resonance spectrum (NMR) was as follows: $^1$H (ppm) from TMS in CDCl$_3$, integral, number of peaks ): 4.00, 6H, s; 2.10, 9H,s; 1.40, 4H, m; 1.00, 3H, m.

Sodium (0.5 g.) was added to a stirred solution of the above triacetate (238 g. in methanol (2.5 2)). The mixture was refluxed, with stirring, for 72 hours. The mixture was evaporated in vacuo.

2-n-Propyl-2-hydroxymethyl-propan-1,3-diol (87 g.) was obtained as colourless crystals (m.pt. 93°).

Ref. W. E. Conrad, L. A. Levasseur, R. F. Murphy, N. L. Hare and H. E. Conrad

J. Org. Chem. 1962, 27, 2227.

A mixture of 2,2-di-(hydroxymethyl)pentan-1-ol(24.6 g), diethyl carbonate (20.1 ml.), potassium hydroxide (0.3 g) and dry ethanol (2 ml) was heated to gentle reflux (oil bath 110°–120°) under a stream of nitrogen for 30 minutes. After this time the ethanol formed was removed by distillation at atmospheric pressure (oil bath 130°–140°, still head temperature 76°). The pressure was reduced to 20 mm. Hg and the oil bath temperature adjusted to 230°. 3hydroxymethyl-3-n-propyloxetane distilled as a colourless liquid (16.7 gms, head temperature 120°–126°).

Gas-liquid chromatography (g.l.c.): OV = 210° produced one peak. Nuclear magnetic resonance spectrum (NMR) was as follows: $^1$H (ppm from TMS in CDCl$_3$, integral, multiplicity): 4.35, 4H, s; 3.60, 2H, m; 1.8–0.7, 7H, m.

3-Ethyl-3-hydroxymethyloxetane was prepared from 2,2-dihydroxymethylbutan-1-ol in an analogous manner.

(ii) Nicotinyl chloride hydrochloride (8.9 gm.) was added to a stirred solution of 3-ethyl-3-hydroxymethyloxetane (5.8 gm.) and dry pyridine (20 ml.) in dry dichloromethane (150 ml.) at 0°. The mixture was stirred at room temperature for 4 days and poured into aqueous sodium carbonate solution. The aqueous mixture was extracted with dichloromethane. The extracts were washed with water and dried over anhydrous magnesium sulphate. The solvent was removed in vacuo. The residue was purified by chromatography on silica eluting with 5% triethylamine in dichloromethane. (3-Ethyloxetan-3-yl)methyl 3-pyridinecarboxylate was obtained as a pale yellow oil (7.0 gm.).

Gas liquid chromatography (g.l.c.): OV210 at 170° produced one peak.

Nuclear magnetic resonance spectrum (NMR) was as follows: $^1$H (p.p.m. from TMS in CDCl$_3$, integral, number of peaks, J$_{Hz}$): 8.20, 1H, m; 7.20, 1H, m; 4.50, 6H, m; 1.80, 2H, m; 1.00, 3H, m.

Infrared spectrum (1R) (liquid film); 1735 cm$^{-1}$.

Mass Spectrum: Chemical ionisation M+1 222.

(iii) Boron trifluoride etherate (1.50 ml.) was added to a stirred solution of (3-ethyl-oxetan-3-yl)methyl 3pyridinecarboxylate) (1.10 gm.) in dry dichloromethane at −70°, under a current of dry nitrogen. The stirred mixture was allowed to warm up to room temperature over a period of six hours. Triethylamine (5 ml) was added and the mixture was poured into water. The aqueous mixture was extracted with dichloromethane. The extracts were washed with water, dried over anhydrous magnesium sulphate and the solvent was removed in vacuo. The residue was purified by chromatography on alumina (Alumina Woelm TSC) eluting with 1:1 dichloromethane:hexane, saturated with ammonia. 4-Ethyl-1-(3-pyridyl)-2,6,7-trioxabicyclo[2.2.2]octane was obtained as colourless crystals (Mpt. 58°–60°, from ether, hexane).

Gas-liquid chromatography (g.l.c.): OV 17 at 170° produced one peak.

In an analogous manner the following compounds were also prepared. (references describe the syntheses of the appropriate carboxylic acids when not available from commercial sources):

4-n-Propyl-1-(3-pyridyl)-2,6,7-trioxabicyclo[2.2.2] octane 4-n-Propyl-1-(4-pyridyl)-2,6,7-trioxabicyclo[2.2.2]octane 4-n-Propyl-1-(2-pyridyl)-2,6,7-trioxabicyclo[2.2.2]octane 4-Cyclohexyl-1-(4-pyridyl)-2,6,7-trioxabicyclo[2.2.2]octane (from 3-cyclohexyl-3-hydroxymethyloxetane which was prepared from 2-cyclohexyl-2-hydroxymethylpropan-1,3-diol in a manner described for the synthesis of 3-hydroxymethyl-3-n-propyloxetane).

1-(5-Bromo-3-pyridyl)-4-n-propyl-2,6,7-trioxabicyclo[2.2.2]octane, T. R. Kelly et al. J. Med. Chem. 1985, 28, 1368

2-(4-Ethyl-2,6,7-trioxabicyclo[2.2.2]oct-1-yl)pyrazine
2,6-Dichloro-4-(4-n-propyl-2,6,7-trioxabicyclo[2.2.2]oct-1-yl)pyrimidine, H. Gershon J. Org. Chem. 1962, 27, 3507

2-(4n-Propyl-2,6,7-trioxabicyclo[2.2.2]oct-1-yl)pyrazine
6-Chloro-3-(4-n-propyl-2,6,7-trioxabicyclo[2.2.2]oct-1-yl)pyridazine, R. F. Homer et al. J. Chem. Soc. 1948, 2195

5-Chloro-2-(4-n-propyl-2,6,7-trioxabicyclo[2.2.2]oct-1-yl)pyrazine, N. Sato and S. Arai J. Het. Chem. 1982, 19, 407

1-Benzyl-4-(4-n-propyl-2,6,7-trioxabicyclo[2.2.2]oct-1-yl)-2-pyrrolidone

1-Methyl-4-(4-n-propyl-2,6,7-trioxabicyclo[2.2.2]oct-1-yl)-2-pyrrolidine

3-Ethyl-5-methyl-4-(4-n-propyl-2,6,7-trioxabicyclo[2.2.2]oct-1-yl)-isoxazole

5-Methyl-4-(4-n-propyl-2,6,7-trioxabicyclo[2.2.2]oct-1yl)oxazole 4-(4n-Propyl-2,6,7-trioxabicyclo[2.2.2]oct-1-yl)thiazole,H. Erlenmeyer et. al. Helv. Chim. Acta. 1945, 28, 362

1-(1,5-Dimethylpyrazol-3-yl)-4-n-propyl-2,6,7-trioxabicyclo [2.2.2]octane, K. Saki et al Chem. Pharm. Bull. (Japan) 1984, 34, 1586

4-Phenyl-1-(4-pyridyl)-2,6,7-trioxabicyclo[2.2.2]octane
4-Cyclohexyl-1-(6iodo-3-pyridyl)-2,6,7-trioxabicyclo[2.2.2 octane

EXAMPLE B

1(6Chloro-3-pyridyl)-4-n-propyl-2,6,7-trioxabicyclo[2.2.2]octane (i) A solution of dicyclohexylcarbodiimide (2.0 gm.) in dry dimethylformamide (5 ml. ) was added to a stirred solution of 6-chloronicotinic acid and 3- hydroxymethyl-3-n-propyloxetane in dry dimethylformamide (15 ml.) at room temperature. The reaction mixture was stirred at room temperature for 60 hours. The mixture was filtered and the solid was washed with diethyl ether (50 ml.). The filtrates were washed with water and then with 5% aqueous sodium carbonate solution. The etheral solution was washed with brine and dried over anhydrous magnesium sulphate. The solvent was removed in vacuo. The residue was purified by chromatography on silica, eluting with 1% triethylamine:-chloroform. (3-n-propyl-oxetan-3-yl)methyl 6-chloro-3-pyridinecarboxylate was obtained as an oil, which solidified on standing (289 mg.).

Gas-liquid chromatography(g.l.c.): OV17 at 240 ° produced one peak.

Nuclear magnetic resonance spectrum (NMR) was as follows: $^1$H (p.p.m.) from TMS in CDCl$_3$, integral, number of peaks, J$_{Hz}$):9.00, 1H, m; 8.20, 1H, m; 7.30, 1H, m; 4.60, 6H, 2.20–0.90, 7H, m.

(ii) 1-(6Chloro-3-pyridyl)-4-n-propyl-2,6,7-trioxabicyclo[2.2.2]octane was prepared from (3-n-propyl-oxetan-3-yl)methyl-6-chloro-3-pyridine-carboxylate using the method described in stage (ii) of Example A.

In an analogous manner the following compounds were also prepared (references described the synthesis of the appropriate carboxylic acids when not available from commercial sources):

1-(6-Chloro-3-pyridyl)-4-cyclohexyl-2,6,7-trioxabicyclo[2.2.2]octane 1-(6-Iodo-3-pyridyl)-4-in-propyl-2,6,7-trioxabicyclo-[2.2.2]-octane, E. Klingsberg. J. Amer. Chem. Soc., 1950, 72, 1031

1-(2,5-Dichloro-4-pyridyl)-4-n-propyl-2,6,7-trioxabicyclo[2.2.2]octane (synthesis ofacid is described below)

1-(2,6-Dichloro-4-pyridyl)-4-n-propyl-2,6,7-trioxabicyclo[2.2.2]octane

4-Cyclohexyl-1-(2,6-dichloro-4-pyridyl)-2,6,7-trioxabicyclo[2.2.2]octane

2,5-Dichloroisonicotic acid n-Butyllithium (14 ml., 1.6M solution in hexane) was added to a stirred solution of 2,5-dichloropyridine (2.8 g.) in dry tetrahydrofuran (60 ml), at −70°, under nitrogen. The reaction mixture was stirred at −70° for 20 minutes and excess solid carbon dioxide was added. The mixture was allowed to warm up to room temperature and then acidified with 2N hydrochloric acid solution. The aqueous mixture was extracted with diethyl ether. The ether extracts were washed with water and dried over anhydrous magnesium sulphate. The solution was evaporated in vacuo. The resulting solid was washed with ethanol.

2,5-Dichloroisonicotinic acid (1.3 g) was obtained as a colourless solid.

Nuclear magnetic resonance spectrum (NMR) was as follows: $^1$H (ppm from TMS in (CD$_3$)$_2$SO, integral, number of peaks: −4.50, 1H, (broad); 8.80, 1H, s; 8.00, 1H, s.

Mass spectrum (MS), chemical ionisation: M+1 192.

Using similar methodology starting from 2,6-dichloropyridine, 2,6-dichloro-4-pyridinecarboxylic acid was prepared.

EXAMPLE C 1-(N-oxo-4-pyridinyl)-4-n-propyl-2,6,7-trioxabicyclo[2.2.2]octane

3-Chloroperbenzoic acid (0.15 gm.) was added to a stirred solution of 4-n-propyl-1-(4-pyridyl)-2,6,7-trioxabicyclo[2.2.2]octane (0.20 gm) in dry chloroform, protected from light. After 6 hours the solution was washed with 0.5N sodium hydroxide solution and then brine. The chloroform extracts were dried over anhydrous magnesium sulpathe. The solvent was removed in vacuo.

1-(N-oxo-4-pyridyl)-4-n-propyl-2,6,7-trioxabicyclo[2.2.2]octane was obtained as a colourless solid (0.18 gm. Mpt 257°).

The following compounds were prepared in an analogous manner:

1-(6-Chloro-N-oxo-3-pyridyl)-4-n-propyl-2,6,7-trioxabicyclo[2.2.2]octane.

1(N-oxo-3-pyridyl)-4-n-propyl-2,6,7-trioxabicyclo[2.2.2]octane.

EXAMPLE D 1-(6Ethynyl-3-pyridyl)-4-n-propyl-2,6,7-trioxabicyclo[2.2.2]octane (i) Bis-triphenylphosphine palladium dichloride (15 mg) and cuprous iodide (5 mg) were added to a stirred solution of 1-(6-iodo-3-pyridyl)-4-n-propyl-2,6,7-trioxabicyclo[2.2.2] octane (430 mg.) and trimethylsilyl acetylene (252 μl) in dry diethylamine (10 ml) under nitrogen. The resulting mixture was stirred at room temperature for 4 hours. The solvent was removed in vacuo and the residue extracted with diethyl ether. The ethereal solution was washed with water, dried over anhydrous magnesium sulphate and evaporated in vacuo. The residue was purified by column chromatography on alumina (Alumina Woelm TSC), eluting with 1:6 dichloromethane:hexane, saturated with ammonia. 4-n-Propyl-1-[6-(2-trimethylsilylethynyl)-3-pyridyl]-2,6,7-trioxabicyclo[2.2.2]octane (282 mg) was obtained as a pale brown crystalline solid.

(ii) Using the methodology described above starting with 1-(6-iodo-3-pyridyl)-4-n-propyl-2,6,7-trioxabicyclo[2.2.2] octane and methyl propargyl ether, 1-[6-(3-methoxyprop-1-ynyl)-3-pyridyl]-4-n-propyl-2,6,7-trioxabicyclo[2.2.2]octane was prepared.

(iii) Tetrabutyl ammonium fluoride solution (0.81 ml, 1M in tetrahydrofuran) was added to a stirred solution of 4-n-propyl-1-[6-(2-trimethylsilylethynyl)-3-pyridyl]-2,6,7-trioxabicyclo[2.2.2]octane (223 mg) in tetrahydrofuran (10 ml.).

The mixture was stirred for 30 minutes at room temperature and the solvent was removed in vacuo and the residue was extracted with diethyl ether. The ethereal solution was washed with water and brine. The ethereal solution was dried over anhydrous magnesium sulphate and evaporated in vacuo.

The residue was purified by chromatography on alumina (Alumina Woelm TSC) eluting with 1:3 dichloromethane:hexane, saturated with ammonia. 1-(6-Ethynyl-3-pyridyl)-4-n-propyl-2,6,7-trioxabicyclo[2.2.2]octane (127 mg.) was obtained as an off-white crystalline solid.

EXAMPLE E

Benzyl 3-(4-n-propyl-2,6,7-trioxabicyclo[2.2.2]oct-1-yl) piperidine-1-carboxylate Using methodology outlined in Example A, starting with 1-(benzyloxycarbonyl)piperidine-3-carbonyl chloride and 3-hydroxymethyl-3-n-propyloxetane, benzyl 3-(4-n-propyl-2,6,7-trioxabicyclo[2.2.2]oct-1-yl)piperidine-1-carboxylate was prepared.

Starting with 1-(benzyloxycarbonyl)piperidine-4-carbonyl chloride (C. Gueremy et. al. J. Med. Chem 1980, 23, 1306) and 3-hydroxymethyl-3-n-propyloxetane, benzyl 4-(4n-propyl-2,6,7-trioxabicyclo[2.2.2]oct-1-yl)piperidine-1-carboxylate was prepared.

EXAMPLE F

3-(4-n-Propyl-2,6,7-trioxabicyclo[2.2.2]oct-1-yl)piperidine

To a solution of benzyl 3-(4n-propyl-2,6,7-trioxabicyclo[2.2.2]oct-1-yl)piperidine-1-carboxylate (7.0 g.) in dry tetrahydrofuran (100 ml) under nitrogen, was added 5% palladium on carbon (0.63 g.) and the system was hydrogenated at atmospheric pressure. When the theoretical volume uptake (450 ml) had been achieved the system was purged with nitrogen and the mixture was filtered through celite. The solution was evaporated in vacuo. The resulting solid was recrystallised from hexane. 3-(4-n-Propyl-2,6,7-trioxabicyclo[2.2.2]oct-1-yl)piperidine (3.3 g.) was obtained as colourless crystals.

Using the above methodology 4-(4-n-propyl-2,6,7-trioxabicyclo[2.2.2]oct-1-yl)piperidine was prepared from benzyl 4-(4n-propyl-2,6,7-trioxabicyclo [2.2.2]oct-1-yl)piperidine-1-carboxylate.

EXAMPLE G

N-Acetyl-3-(4-n-propyl-2,6,7-trioxabicyclo[2.2.2]oct-1-yl)piperidine

Acetyl chloride (81 µl) was added to a stirred solution of 3-(4n-propyl-2,6,7-trioxabicyclo[2.2.2]oct-1-yl)piperidine (0.25 g.) and pyridine (92 µl) in dichloromethane (15 ml) at 0°. The mixture was stirred at room temperature for 3 hours. The mixture was washed with water, saturated aqueous sodium hydrogen carbonate solution and finally brine. The dichloromethane extracts were dried over anhydrous magnesium sulphate and evaporated in vacuo. The residue was purified by chromatography on alumina (Alumina Woelm TSC) eluting with 1:3 dichlormethane:hexane, saturated with ammonia. N-Acetyl- 3-(4-n-propyl-2,6,7-trioxabicyclo[2.2.2]oct-1-yl)piperidine (0.15 g.) was obtained as a colourless oil.

Starting from 3-(4-n-propyl-2,6,7-trioxabicyclo[2.2.2]oct-1-yl)piperidine and methyl chloroformate, methyl 3-(4n-propyl-2,6,7-trioxabicyclo[2.2.2]oct-1-yl)piperidine-1-carboxylate was prepared.

Starting from 4-(4n-propyl-2,6,7-trioxabicyclo[2.2.2]oct-1-yl)piperidine and acetal chloride or methyl chloroformate, N-acetyl-4-(4-n-propyl-2,6,7-trioxabicyclo[2.2.2]oct-1-yl)piperdine and methyl 4-(4-n-propyl-2,6,7-trioxabicyclo[2.2.2]oct-1-yl)piperidine-1-carboxylate were prepared.

EXAMPLE H

2-(4-n-Propyl-2,6,7-trioxabicyclo[2.2.2]oct-1-yl)pyrrole i) A solution of pyrrole-2-carboxylic acid (0.5 g.) and thionyl chloride (2.0 ml) in benzene (20 ml) was refluxed for 2 hours. The mixture was cooled and evaporated in vacuo. Dry benzene (10 ml.) was added to the resulting acid halide. 3-Hydroxymethyl-3-n-propyloxetane (1.2 g.) in dry benzene (10 ml) was added and was followed by dry pyridine (1.0 ml). The reaction mixture was stirred for 24 hours at room temperature. The reaction mixture was poured into aqueous sodium hydrogen carbonate solution. The aqueous mixture was extracted with dichloromethane. The extracts were washed with water and dried over anhydrous magnesium sulphate. The solvent was removed in vacuo. The residue was purified by chromatography on silica, eluting with 5% triethylamine in dichloromethane. (3-n-Propyloxetan-3-yl)methyl 2-pyrrolecarboxylate (0.7 g) was obtained as a colourless oil.

Nuclear magnetic resonance spectrum (NMR) was as follows: $^1$H (p.p.m.) from TMS in CDCl$_3$, integral, number of peaks): 6.90, 2H, m; 6.10, 1H, m; 4.60–4.20, 6H, m; 2.00–0.80, 7H, m.

Using methodology described in stage (ii) of Example A and starting from (3-n-propyloxetan-3-yl)methyl 2pyrrolecarboxylate, 2-(4-n-propyl-2,6,7-trioxabicyclo[2.2.2]oct-1-yl)pyrrole was obtained.

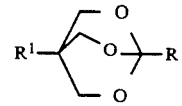

| Compound No. | R | R$^1$ | mpt | Mass Spectrum Chemical Ionisation M + 1 | Synthetic Method | Nuclear Magnetic Resonance Spectrum |
|---|---|---|---|---|---|---|
| 1 | 3-pyridyl | Et | 58–60° | 222 | A | 7.90,1H,m;7.20,1H,m;4.25,6H,s;1.60, 2H,m;1.20,3H,m |
| 2 | 3-pyridyl | n-Pr | 65.6° | 236 | A | 8.90,1H,m;8.55,1H,m- ;7.90,1H,m; 7.20,1H,m;4.10,6H,s;1.60–0.90,7H,m |
| 3 | 6-chloro-3-pyridyl | n-Pr | 119° | 270 | B | 8.60,1H,m;7.80,1H,m;7.20,1H,m;4.10, 6H,s;1.60–0.80,7H,m |
| 4 | 6-chloro-1-oxo-3-pyridyl | n-Pr | 120–3° | 286 | C | 8.60,1H,m;7.40,2H,m;4.10,6H,s;1.30, 4H,m;0.90,3H,m |
| 5 | 6-chloro-3-pyridyl | c.hex | solid | 310 | B | 8.60,1H,m;7.85,1H,m;7.30,1H,m;4.10, 6H,s;2.00–0.90,11H,m |
| 6 | 4-pyridyl | n-Pr | 155° | 236 | A | 8.80,2H,m;7.50,2H,m;4.10,6H,m;1.50–0.80,7H,m |
| 7 | 1-oxo-4-pyridyl | n-Pr | 257° | 252 | C | 8.10,2H,d,8;7.40,2H,d,8;4.10,6H,s; 1.60–0.90,7H,m |
| 8 | 4-pyridyl | c.hex | solid | 276 | A | 8.60,2H,m;7.50,2H,m;4.15,6H,s;2.00–0.90,11H,m |
| 9 | 2-pyridyl | n-Pr | solid | 236 | A | 8.40,1H,m;7.70,2H,m;7.20,1H,m;4.20, 6H,s;1.50–0.80,7H,m |
| 10 | 5-bromo-3-pyridyl | n-Pr | 78–80° | 314 316 | A | 8.75,1H,m;8.65,1H,m;8.05,1H,m; 4.10,6H,s;1.25,4H,m;0.95,3H,m |

-continued

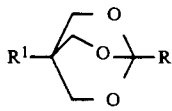

| Compound No. | R | R¹ | mpt | Mass Spectrum Chemical Ionisation M + 1 | Synthetic Method | Nuclear Magnetic Resonance Spectrum |
|---|---|---|---|---|---|---|
| 11 | 6-iodo-3-pyridyl | n-Pr | solid | 362 | B | 8.50,1H,m;7.50,2H,s;4.10,6H,s;1.20, 4H,m;1.00,3H,m |
| 12 | 2,5-dichloro-4-pyridyl | n-Pr | solid | 304 | B | 8.40,1H,s;7.70,1H,s;4.10,6H, s;2.00–0.90,7H,m |
| 13 | 2,6-dichloro-4-pyridyl | n-Pr | solid | 304 | B | 7.40,2H,s;4.10,6H,s;1.20,4H,m;0.90, 3H,m |
| 14 | 6-ethynyl-3-pyridyl | n-Pr | solid | 260 | D | 8.70,1H,m;7.80,1H,m;7.40,1H,m;4.10, 6H,s;3.20,1H,s;1.20,4H,m;1.00,3H,m |
| 15 | 6-(2-trimethyl-silylethynyl)-3-pyridyl | n-Pr | solid | 332 | D | 8.70,1H,m;7.80,1H,m;7.30,1H,m;4.10, 6H,s;1.30,4H,m;1.00,3H,m;0.30,9H,s |
| 16 | 2-pyrazinyl | Et | solid | 223 | A | 9.00,1H,m;8.60,2H,m;4.10,6H,s;1.40, 2H,m;0.90,3H,m |
| 17 | 2-pyrazinyl | n-Pr | solid | 237 | A | 8.90,1H,m;8.60,2H,m;4.20,6H,s;1.30, 4H,m;0.95,3H,m |
| 18 | 2,6-dichloro-4-pyrimidinyl | n-Pr | solid | 305 | A | 7.65,1H,s;4.15,6H,s;1.20,4H,m; 0.95,3H,m |
| 19 | 3-chloro-6-pyridazinyl | n-Pr | solid | 271 | A | 7.80,1H,d,6;7.55,1H,d,6;4.20,6H,s; 1.25,4H,m;0.90,3H,m |
| 20 | 3-ethyl-5-methyl-4-isoxazolyl | n-Pr | Oil | 268 | A | 4.10,6H,s;2.90,2H,q,6;2.60,3H,s; 1.60–1.00,10H,m |
| 21 | 5-methyl-4-oxazolyl | n-Pr | 114° | 240 | A | 7.70,1H,s;4.10,6H,s;1.20,4H,m;0.90, 3H,m |
| 22 | 1-benzyl-2-oxo-4-pyrrolidinyl | n-Pr | 97° | 332 | A | 7.30,5H,s;4.60,2H,s;4.00,6H,s;3.50–2.50,5H,m;1.40–0.80,7H,m |
| 23 | 1-methyl-2-oxo-4-pyrrolidinyl | n-Pr | 116° | 256 | A | 4.00,6H,s;3.60–2.80,8H,m;1.60–0.80, 7H,m |
| 24 | 6-(3-methoxyprop-1-ynyl)-3-pyridyl | n-Pr | 126° | 304 | D | 7.90,1H,m;7.45,1H,m;4.35,2H,s;4.10, 6H,s;3.45,3H,s;1.25,4H,m;0.95,3H,m |
| 25 | 1-(benzyloxy carbonyl)-3-piperidinyl | n-Pr | solid | 376 | E | 7.40,5H,s;5.20,2H,s;4.60–4.10,2H,m; 4.00,6H,s;3.00–2.50,2H,m;2.20–0.80,12H,m |
| 26 | 3-piperidinyl | n-Pr | solid | 242 | F | 3.90,6H,s;3.20–2.20,5H,m;2.00–0.80, 12H,m |
| 27 | 1-acetyl-3-piperidinyl | n-Pr | oil | 284 | G | 4.70–4.20,2H,m;3.90,6H,s;3.00,2H,m; 2.10,3H,s;1.80–0.80,12H,m |
| 28 | 1-methoxycarbonyl-3-piperidinyl | n-Pr | solid | 300 | G | 4.10,2H,m;3.90,6H,s;3.60,3H,s;2.60, 2H,m;2.00–0.90,12H,m |
| 29 | 1-(benzyloxy carbonyl)-4-piperidinyl | n-Pr | solid | 376 | E | 7.30,5H,s;5.00,2H,s;4.15,2H,m;3.80, 6H,s;2.60,2H,m;1.80–0.75,12H,m |
| 30 | 4-piperidinyl | n-Pr | solid | 242 | F | 3.90,6H,s;3.10,2H,m;2.50,2H,m;1.80–0.80,13H,m |
| 31 | 1-acetyl-4-piperidinyl | n-Pr | solid | 284 | G | 4.60,2H,m;3.90,6H,s;3.00,2H,m;2.10, 3H,s;2.00–0.75,12H,m |
| 32 | 1-methoxycarbonyl-4-piperidinyl | n-Pr | solid | 300 | G | 4.10,2H,m;3.80,6H,s;3.60,3H,s;2.60, 2H,m;2.00–0.80, 2H,m |
| 33 | 4-thiazolyl | n-Pr | solid | 242 | A | 8.80,1H,m;7.60,1H,m;4.20,6H,s;1.25, 4H,m;0.95,3H,m |
| 34 | 2-pyrrolyl | n-Pr | 129° | 224 | H | 6.80,1H,m;6.40,1H,m;6.20,1H,m;4.20, 6H,s;1.40,4H,m;1.20,3H,m |
| 35 | 1-oxo-3-pyridyl | n-Pr | 151° | 252 | C | 8.45,1H,m;8.15,1H,m;7.45,1H,m;7.20, 1H,m;4.10,6H,s;1.25,4H,m;0.95,3H,m |
| 36 | 5-chloro-2-pyrazinyl | n-Pr | solid | 271 | A | 8.72,1H,s;8.60,1H,s;4.15,6H,s;1.25, 4H,m;0.95,3H,m |
| 37 | 2,6-dichloro-4-pyridyl | c.hex | solid | 344 | B | 7.50,2H,s;4.15,6H,s;2.00–0.80,11H,m |
| 38 | 1,5-dimethyl-pyrazol-3-yl | n-Pr | 184° | 253 | A | 6.16,1H,s;4.10,6H,s;3.78,3H,s;2.24, 3H,s;1.20–1.30,4H,m;0.94,3H,t,5 |
| 39 | 4-pyridyl | Phenyl | 220° | 270 | A | 8.70,2H,d,7;7.60,2H,d,7;7.40,3H,m; 7.20,2H,m; 4.50,6H,s. |
| 40 | 6-iodo-3-pyridyl | c.hex | 253° | 402 | A | 8.55,1H,m;7.65,1H,d,7Hz;7.50,1H,m; 4.10,6H,s;2.00–0.90,11H,m. |

A. Lethal Activity Against Houseflies.

The activity of compounds of the invention against unanaesthetised female *Musca domestica* (WRL strain) was demonstrated by topical application to the test insect of a solution of the compound under test in butanone, either on its own or in conjunction with 6 μg piperonyl butoxide.

The activity of the compounds under test were assessed at 15 mins. 1 day and 2 days.

The following compounds were active at less than 30 μg/fly: 6; 3; 5; 8; 11;13.

The following compounds were active at less than 1 μg/fly, when applied in conjunction with the synergist, piperonyl butoxide: 15; 14.

B. Lethal Activity Against *Sitophilus granarius*

The activity of the compounds of the invention against *S. granarius* adults was demonstrated by the addition of the compound in acetone solution to grain, to which the insects were later infested. Mortality was assessed after 6 days.

The following compounds gave activity at concentrations of less than 200 ppm in grain: 3; 7; 5; 9; 8; 11; 24; 13.

The following compounds gave activity at concentrations of less than 50 ppm in grain; 15; 14.

C. The Lethal Activity Against *Culex quinquefasciatus*

The activity of the compounds of the invention against female Culex adults was demonstrated by direct spraying of 0.2 ml of the compound in OPD/methylene chloride. Mortality was assessed after 25 hours.

The following compounds were active at less than 1%: 6; 3; 5; 11.

The following compounds were active at less than 0.3%: 15; 14.

D. Lethal Activity Against *Blattella germanica*

The activity of compounds of the invention against anaesthtised male *Blattella germanica* (WRL strain) was demonstrated by the topical application to the test insect of a solution of the compound under test in butanone.

The activity of the test compound was assessed when applied topically in conjunction with the synergist piperonyl butoxide. Mortality was assessed after 24 and 48 hours.

The following compounds were active at less than 50 μg/insect: 3; 4; 6; 7.

The following compounds were active at less than 5 μg/insect; 5; 8.

Mammalian toxicity of compounds of the invention was determined in mice. For both compounds 5 and 11 the $LD_{50}$ in mice was greater than 200 mg/kg.

| Formulations | | |
|---|---|---|
| 1. Emulsifiable Concentrate | | |
| Compound of formula (I) | 10.00 | |
| Ethlan KEO | 20.00 | |
| Xylene | 67.50 | |
| Butylated Hydroxyanisole | 2.50 | |
| | 100.00 | |
| 2. Wettable Powder | | |
| Compound of formula (I) | 25.0 | |
| Attapulgite | 69.50 | |
| Sodium isopropylbenzene sulphonate | 0.50 | |
| Sodium salt of condensed naphthalene sulphonic acid | 2.50 | |
| Butylated hydroxytoluene | 2.50 | |
| | 100.00 | |
| 3. Dust | | |
| Compound of formula (I) | 0.50 | |
| Butylated Hydroxyanisole | 0.10 | |
| Talc | 99.40 | |
| | 100.00 | |
| 4. Bait | | |
| Compound of formula (I) | 40.25 | |
| Icing Sugar | 59.65 | |
| Butylated hydroxy toluene | 0.10 | |
| | 100.00 | |
| 5. Lacquer | | |
| Compound of formula (I) | 2.5 | |
| Resin | 5.0 | |
| Butylated Hydroxy anisole | 0.5 | |
| High aromatic white spirit | 92.0 | |
| | 100.00 | |
| 6. Aerosol | | |
| Compound of formula (I) | 0.30 | |
| Butylated Hydroxy anisole | 0.10 | |
| 1,1,1-Trichloroethane | 4.00 | |
| Odourless Kerosene | 15.60 | |
| Arcton 11/12. 50:50 mix | 80.00 | |
| | 100.00 | |
| 7. Spray | | |
| Compound of formula (I) | 0.1 | |
| Butylated Hydroxy anisole | 0.1 | |
| Xylene | 10.0 | |
| Odourless Kerosene | 89.8 | |
| | 100.00 | |
| 8. Potentiated Spray | | |
| Compound of formula (I) | 0.1 | |
| Piperonyl Butoxide | 0.1 | |
| Butylated Hydroxyanisole | 0.1 | |
| Xylene | 10.1 | |
| Odourless Kerosene | 89.2 | |
| | 100.0 | |

We claim:
1. A compound of the formula (I):

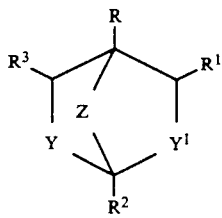

wherein
R is $C_{2-10}$ alkyl, $C_{2-10}$ alkenyl or $C_{2-10}$ alkynyl or $C_{1-10}$ alkyl, $C_{2-10}$ alkenyl or $C_{2-10}$ alkynyl substituted by cyano, halogen, $C_{3-4}$ cycloalkyl, $C_{1-4}$ alkoxy or a group $S(O)mR^4$ where $R^4$ is $C_{1-4}$ alkyl optionally substituted by halogen and m is 0, 1 or 2, or R is $C_{3-10}$ cycloalkyl, $C_{4-10}$ cycloalkylalkyl, $C_{4-10}$ cycloalkenyl or phenyl, each optionally substituted by $C_{1-4}$ alkoxy, $C_{1-3}$ alkyl, $C_{2-4}$ alkynyl, halogen, cyano or a group $S(O)mR^4$ as hereinbefore defined;

$R^1$ is hydrogen, $C_{1-3}$ alkyl, $C_{2-3}$ alkenyl or alkynyl, each optionally substituted by halo, cyano, $C_{1-4}$ alkoxy, alkyl carbalkoxy containing up to 6 carbon atoms or a group $S(O)mR^4$ as hereinbefore defined, or $R^1$ is cyano, $CO_2R^4$ wherein $R^4$ is as hereinbefore defined or gem dimethyl; or $R^1$ and R and the carbon atoms to which they are attached form a $C_{5-7}$ carbocyclic ring optionally substituted by cyano, halogen, $C_{1-3}$ alkyl, $C_{2-3}$ alkoxy or alkenyl;

$R^2$ is a pyridine, piperdine or pyrrole or one of these rings substituted by hydroxy, oxo, halo, cyano, imino or amino or hydroxy, oxo, halo, cyano, imino or amino substituted by $C_{1-4}$ alkyl or $C_{1-4}$ acyl or $C_{1-6}$ carbalkoxy; azido, nitro, formyl, $C_{1-6}$ carbalkoxy, thiocyanante, $C_{1-4}$ acyl, $C_{1-4}$ acyloxy, $C_{1-4}$ alkoxyiminiomethylene, $C_{1-4}$ acyloxyiminomethylene, or $C_{1-3}$ alkyl or alkoxy each optionally substituted by halo; or $C_{2-3}$ alkenyl or ethynyl each optionally substituted by cyano, a $C_{1-9}$ aliphatic group optionally substituted by hydroxy, $C_{1-4}$ alkoxy, $C_{1-4}$ acyloxy, $C_{1-4}$ acylthio or halogen, a group —CO.R$^7$ where R$^7$ is $C_{1-6}$ hydrocarbyl or hydrocarbyloxy group or an amino group optionally substituted by one or two $C_{1-4}$ alkyl groups; or by a silyl group substituted by three $C_{1-4}$ alkyl groups or two $C_{1-4}$ alkyl groups and a phenyl group; and R$^3$ is hydrogen, cyano, $C_{1-3}$ alkyl, $C_{2-3}$ alkenyl or alkynyl, each optionally substituted by cyano, $C_{1-4}$ alkoxy, halo or a group $S(O)mR^4$ as hereinbefore defined, Y and Y$^1$ are oxygen;

Z is CH$_2$O.

2. The compound according to claim 1 wherein R is an n-propyl, n-butyl, i-butyl, t-butyl, cyclohexyl or phenyl group.

3. The compound according to claim 1 wherein R$^1$ is hydrogen or a methyl, cyano, trifluoromethyl or ethyl group.

4. The compound according to claim 1 wherein the R$^2$ ring is substituted by hydroxy; oxo; halo; cyano; imino or amino optionally substituted by $C_{1-4}$ alkyl or acyl or $C_{1-6}$ carbalkoxy; azido; nitro; formyl; $C_{1-6}$ carbalkoxy; thiocyanate; $C_{1-4}$ acyl; $C_{1-4}$ acyloxy, $C_{1-4}$ alkoxyiminomethylene; $C_{1-4}$ acyloxyiminomethylene; or $C_{1-3}$ alkyl or alkoxy each optionally substituted by halo; or $C_{2-3}$ alkenyl or ethynyl each optionally substituted by cyano, a $C_{1-9}$ aliphatic group optionally substituted by hydroxy, $C_{1-4}$ alkoxy, $C_{1-4}$ acyloxy, $C_{1-4}$ acylthio or halogen, a group —CO.R$^7$ is a $C_{1-6}$ hydrocarbyl or hydrocarbyloxy group or an amino group optionally substituted by one or two $C_{1-4}$ alkyl groups; or by a silyl group substituted by three $C_{1-4}$ alkyl groups or two $C_{1-4}$ alkyl groups and a phenyl group.

5. The compound according to claim 1 wherein R$^2$ includes a 3- or 4-pyridyl ring.

6. The compound according to claim 1 wherein R$^3$ is hydrogen.

7. The compound according to claim 1 which is 1-(6-Chloro-3-pyridyl)-4-n-propyl-2,6,7-trioxabicyclo[2.2.2]octane 1-(6-Chloro-N-oxo-3-pyridyl)-4-n-propyl-2,6,7-trioxabicyclo[2.2.2]octane 1-(6-Chloro-3-pyridyl)-4-cyclohexyl-2,6,7-trioxabicyclo[2.2.2]octane 4-n-Propyl-1-(4-pyridyl)-2,6,7-trioxabicyclo[2.2.2]octane 1-(N-Oxo-4-pyridyl)-4-n-propyl-2,6,7-trioxabicyclo[2.2.2]octane 4-Cyclohexyl-1-(4-pyridyl)-2,6,7-trioxabicyclo[2.2.2]octane 1-(6-Iodo-3-pyridyl)-4-n-propyl-2,6,7-trioxabicyclo[2.2.2]octane 1-(2,6-Dichloro-4-pyridyl)-4-n-propyl-2,6,7-trioxabicyclo[2.2.2]octane 1-(4-Ethynyl-3-pyridyl)-4-n-propyl2,6,7-trioxabicyclo[2.2.2]octane 4-n-Propyl-1-[6-(2-trimethylsilylethynyl)-3-pyridyl-2,6,7-trioxabicyclo[2.2.2]octane 1-[6-(3-Methoxyprop-1-ynyl)-3-pyridyl]-4-n-propyl-2,6,7-trioxabicyclo[2.2.2]octane 4-Phenyl-1-(4-pyridyl)-2,6,7-trioxabicyclo[2.2.2]octane 4-Cyclohexyl-1-(6-iodo-3-pyridyl)-2,6,7-trioxabicyclo[2.2.2]octane 8. A pesticidal composition comprising as active ingredient, a compound according to claim 1 in admixture with a carrier or diluent.

9. A compound according to claim 1 of the formula:

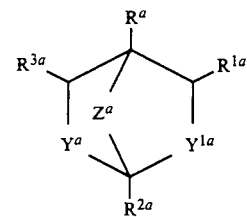

wherein R$^a$ is C$_{2-10}$ alkyl, alkenyl or alkynyl, each optionally substituted by cyano, halogen, $C_{1-4}$ alkoxy or a group $S(O)mR^{4a}$ where R$^{4a}$ is $C_{1-4}$ and m is 0, 1 or 2, or R$^a$ is C$_{3-10}$ cycloalkyl, C$_{4-10}$ cycloalkenyl or phenyl, each optionally substituted by $C_{1-4}$ alkoxy, $C_{1-3}$ alkyl, $C_{2-4}$ alkynyl, halogen, cyano or a group $S(O)mR^{4a}$; R$^{1a}$ is hydrogen, $C_{1-3}$ alkyl, $C_{2-3}$ alkenyl or alkynyl, each optionally substituted by halo, cyano, $C_{1-4}$ alkoxy, alkyl, carbalkoxy containing up to 6 carbon atoms or a group $S(O)mR^{4a}$ as hereinbefore defined, or R$^{1a}$ is cyano or gem dimethyl; or R$^{1a}$ and R$^a$ and the carbon atoms to which they are attached form a C$_{5-7}$ carbocyclic ring optionally substituted by $C_{1-3}$ alkyl, $C_{2-3}$ alkoxy or alkenyl; R$^{2a}$ is a pyridine, piperidine or one of these rings hydroxy, oxo, halo, cyano, imino or amino or hydroxy, oxo, halo, cyano, imino or amino substituted by $C_{1-4}$ alkyl or acyl or $C_{1-6}$ carbalkoxy; azido, nitro, formyl, $C_{1-6}$ carbalkoxy, thiocyanate, $C_{1-4}$ acyl, $C_{1-4}$ acyloxy, $C_{1-4}$ alkoxyiminomethylene, $C_{1-4}$ acyloxyiminomethylene, or $C_{1-3}$ alkyl or alkoxy each optionally substituted by halo; or $C_{2-3}$ alkenyl or ethynyl each optionally substituted by cyano, a $C_{1-9}$ aliphatic group optionally substituted by hydroxy, $C_{1-4}$ alkoxy, $C_{1-4}$ acyloxy, $C_{1-4}$ acylthio or halogen, a group —CO.R$^7$ where R$^7$ is a $C_{1-6}$ hydrocarbyl or hydrocarbyloxy group or an amino group optionally substituted by one or two $C_{1-4}$ alkyl groups; or by a silyl group substituted by three $C_{1-4}$ alkyl groups or two $C_{1-4}$ alkyl groups and a phenyl group and R$^{3a}$ is hydrogen, cyano, $C_{1-3}$ alkyl, $C_{2-3}$ alkenyl or alkynyl, each optionally substituted by cyano, $C_{1-4}$ alkoxy, halo or a group $S(O)mR^{4a}$ as hereinbefore defined, Y$^a$ and Y$^{1a}$ are oxygen Z$^a$ is CH$_2$O.

* * * * *